United States Patent
Peterson et al.

(10) Patent No.: US 9,465,042 B2
(45) Date of Patent: Oct. 11, 2016

(54) TAPE ADAPTOR

(75) Inventors: Bruce Peterson, Alexandria, MN (US); Brent Urke, Alexandria, MN (US)

(73) Assignee: DOUGLAS SCIENTIFIC, LLC, Alexandria, MN (US)

(*) Notice: Subject to any disclaimer, the term of this patent is extended or adjusted under 35 U.S.C. 154(b) by 904 days.

(21) Appl. No.: 12/864,516

(22) PCT Filed: Jan. 23, 2009

(86) PCT No.: PCT/US2009/031755
§ 371 (c)(1),
(2), (4) Date: Jul. 26, 2010

(87) PCT Pub. No.: WO2009/094495
PCT Pub. Date: Jul. 30, 2009

(65) Prior Publication Data
US 2010/0303689 A1    Dec. 2, 2010

Related U.S. Application Data

(60) Provisional application No. 61/023,845, filed on Jan. 26, 2008.

(51) Int. Cl.
*B01L 3/00* (2006.01)
*G01N 35/00* (2006.01)
*B01L 9/00* (2006.01)

(52) U.S. Cl.
CPC ..... *G01N 35/00009* (2013.01); *B01L 3/50855* (2013.01); *B01L 3/545* (2013.01); *B01L 9/523* (2013.01); *B01L 2200/025* (2013.01); *B01L 2300/123* (2013.01)

(58) Field of Classification Search
CPC ..................................................... B01L 3/5085
USPC .................................... 422/553, 552, 551
See application file for complete search history.

(56) References Cited

U.S. PATENT DOCUMENTS

| 6,878,345 | B1 | 4/2005 | Astle |
| 2002/0070173 | A1* | 6/2002 | Otto et al. ............... 210/695 |
| 2004/0071599 | A1 | 4/2004 | Rusch et al. |
| 2007/0297950 | A1 | 12/2007 | Hochstrasser et al. |

* cited by examiner

*Primary Examiner* — Natalia Levkovich
(74) *Attorney, Agent, or Firm* — Greenberg Traurig LLP

(57) ABSTRACT

A tape adaptor (8) includes a bottom plate (20) and a top plate (60) mounted to the bottom plate (20) with a space (40) defined between an upper side wall (26) of the bottom plate (20) and a lower face (68) of the top plate (60) for receiving a tape segment (100) remaining on or cut from a continuous array tape (10). The tape segment (100) includes an array of wells (54) between two edges (52). A slit (46) is formed between an end (62) of the top plate (60) and an end (22) of the bottom plate (20). The tape segment (100) is slideably extended through the slit (46) into the space (40) with the edges (52) sliding on two ridges (38) on two longitudinal edges (36) of the bottom plate (20). The bottom plate (20) can include at least one groove (30) to receive the array of wells (54) of the tape segment (100). The tape segment (100) is positioned relative to the tape adaptor (8) by the ridges (38) or the groove (30).

20 Claims, 6 Drawing Sheets

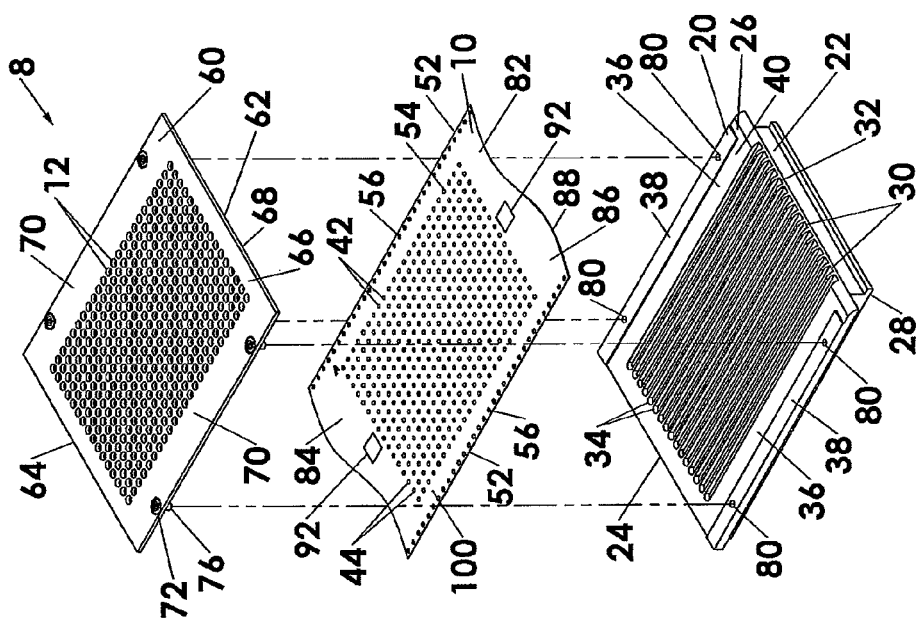
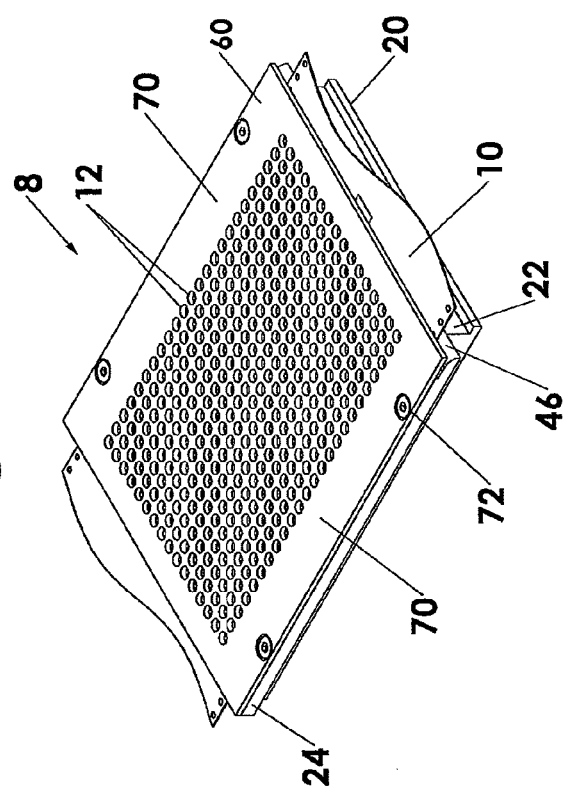

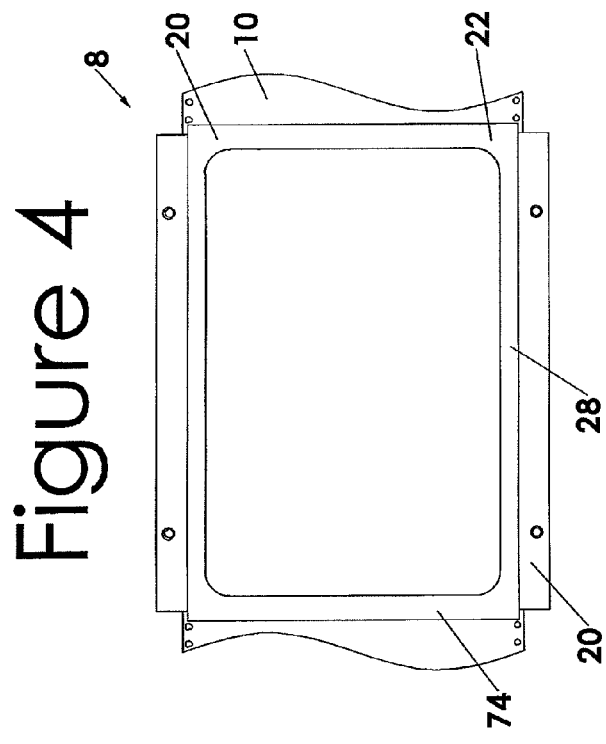
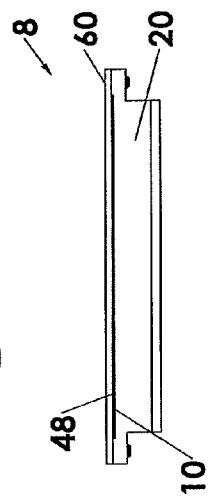
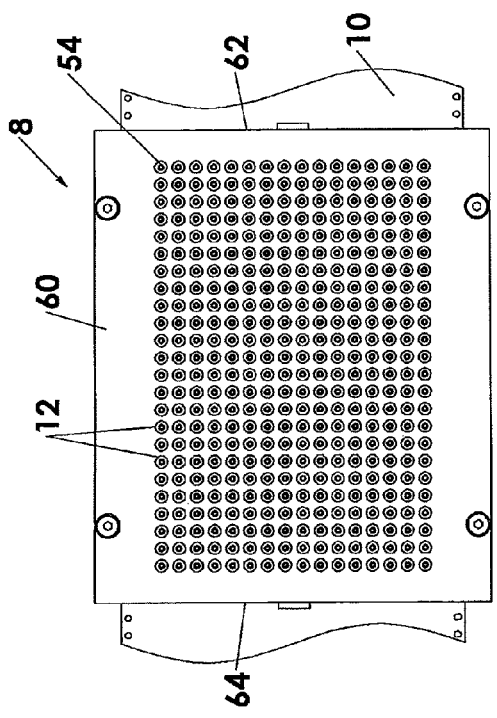
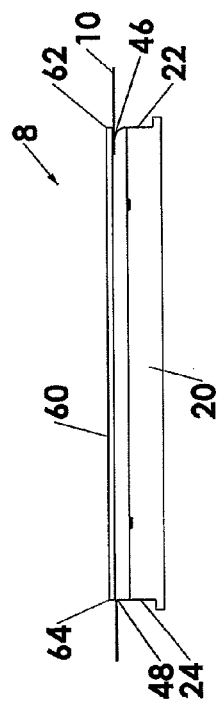

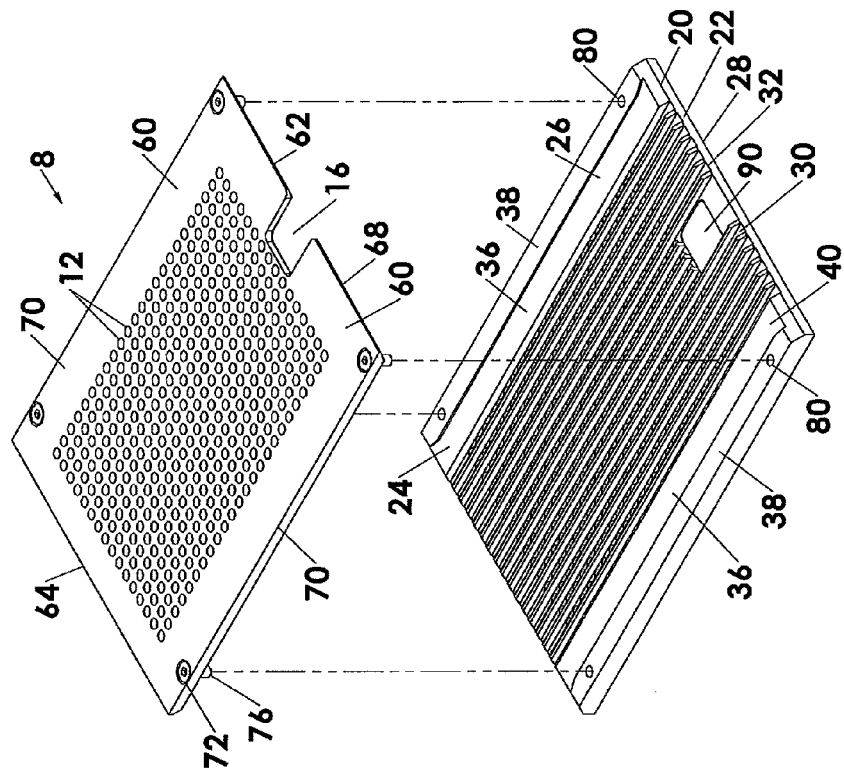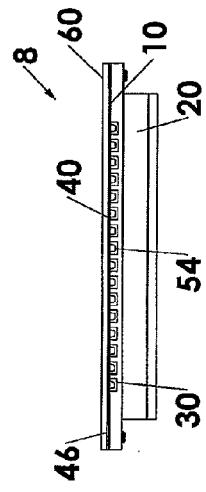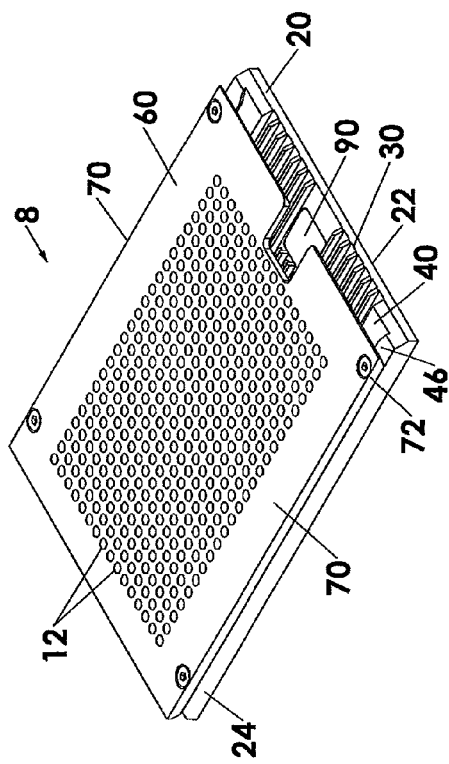

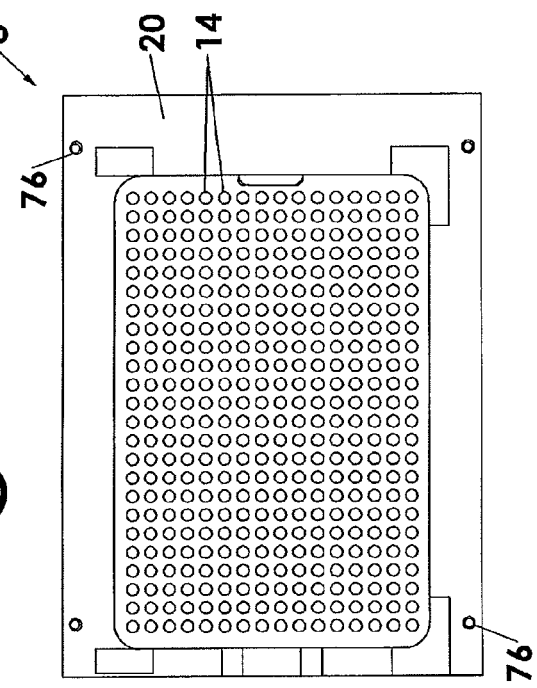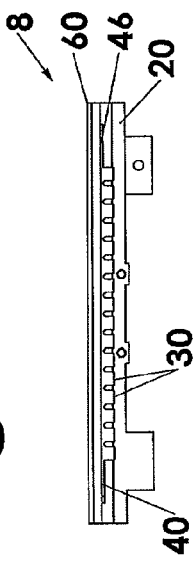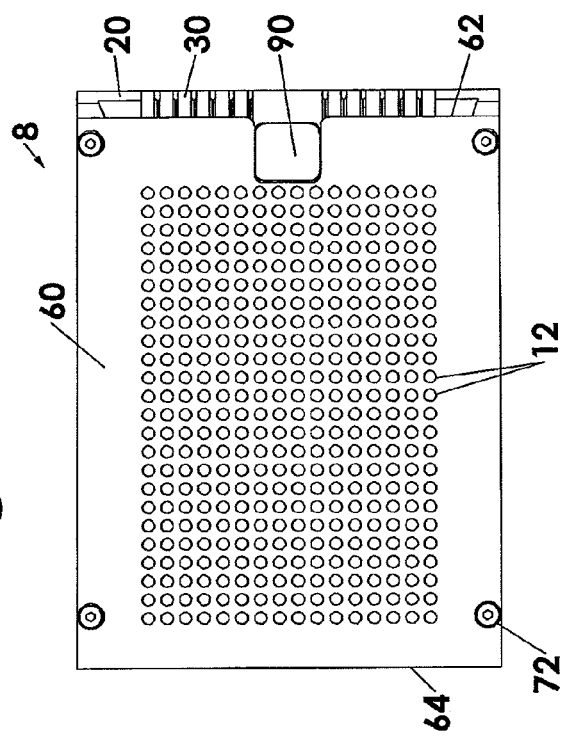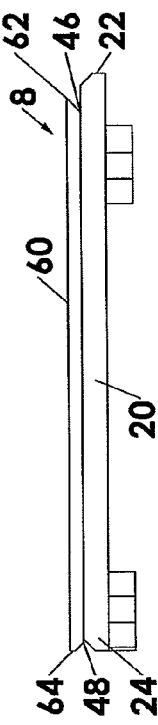

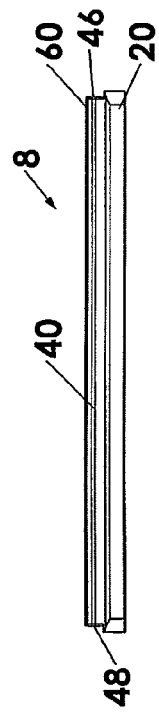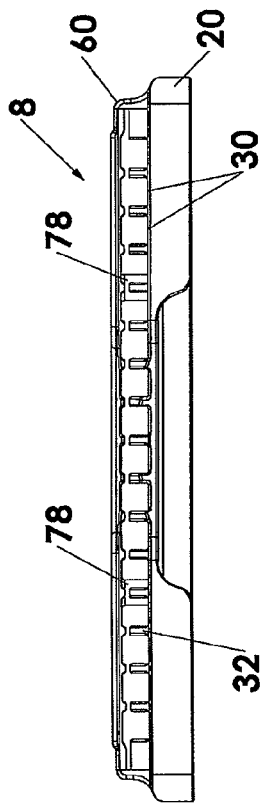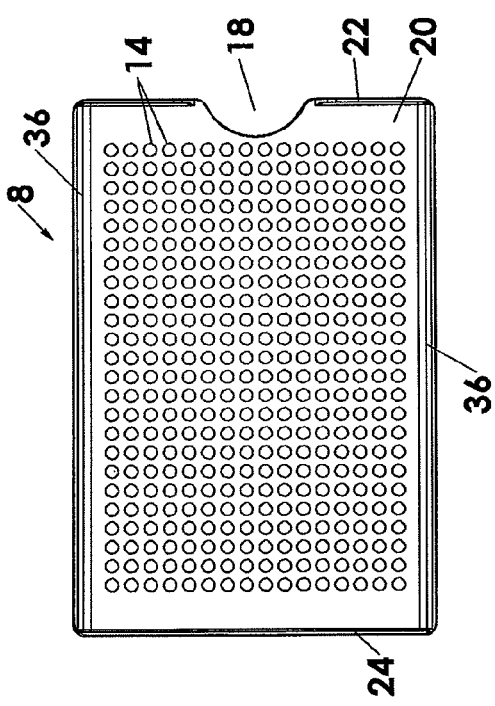

TAPE ADAPTOR

This application is a National Stage entry of International Application No. PCT/US2009/31755, entitled "TAPE ADAPTOR" filed Jan. 23, 2009, which claims benefit under U.S.C. §119(e) of U.S. Provisional Application No. 61/023,845, entitled "Tape Adaptor," filed Jan. 26, 2008.

This application is a national stage entry of PCT/US09/31755 with the International Filing Date of Jan. 23, 2009 that claims priority from U.S. Provisional Application 61/023,845, filed Jan. 26, 2008.

BACKGROUND OF THE INVENTION

The present invention relates to a tape adaptor and, more particularly, to a tape adaptor for changing the characteristics of a continuous array tape to those of a microtiter plate.

Microtiter plates, also known as trays or microplates, generally include an array of wells for sample storage and retrieval or for qualitative and quantitative assays in various biological research and clinical diagnostic procedures. These microtiter plates may or may not conform to the Society of Biomolecular Sciences published microplate standards. There is a considerable quantity of equipment or instruments in the industry that utilize microtiter plates. Another manner of containing reagents and samples is a continuous array tape. However, the continuous array tape can not be directly handled by the existing equipment or instruments for microtiter plates.

Thus, a need exists for making a continuous array tape to have characteristics of a microtiter plate that can be utilized on existing equipment or instruments for microtiter plates and that conforms to the Society of Biomolecular Sciences published microplate standards.

BRIEF SUMMARY OF THE INVENTION

The present invention solves this need and other problems in the field of microtiter plates by providing, in a preferred form, a tape adaptor including a bottom plate having first and second ends spaced in a first direction and upper and lower side walls extending between the first and second ends. The upper and lower side walls of the bottom plate are spaced in a second direction perpendicular to the first direction. The bottom plate further includes two edges extending between the first and second ends and spaced in a third direction perpendicular to the first and second directions. The upper side wall of the bottom plate further includes two ridges extending along the longitudinal edges and extending away from the lower side wall of the bottom plate in the second direction. A top plate includes first and second ends spaced in the first direction and upper and lower faces extending between the first and second ends of the top plate. The upper and lower faces of the top plate are spaced in the second direction. The top plate is mounted to the upper side wall of the bottom plate, defining a space between the upper side wall of the bottom plate and the lower face of the top plate for receiving a tape segment remaining on or cut from a continuous array tape. The tape segment includes an array of wells and two edges on two sides of the array of wells and spaced from the array of wells in the third direction. The tape segment is slideably extended through the first slit in the first direction into the space with the edges of the tape segment slideable on the ridges of the bottom plate. The tape segment can be positioned relative to the top and bottom plates by friction between the ridges of the bottom plate and the edges of the tape segment.

In preferred forms, the bottom plate includes a plurality of grooves extending from the upper side wall towards but spaced from the lower side wall in the second direction. The grooves are intermediate the first and second longitudinal edges of the bottom plate. Furthermore, the grooves are parallel to each other in the first direction and spaced from each other in the third direction. The grooves have a number corresponding to the rows of the array of wells of the tape segment. The array of wells of the tape segment has a plurality of columns spaced in the first direction and a plurality of rows spaced in the third direction. The plurality of rows of the array of wells of the tape segment are received in the plurality of grooves. The tape segment can be positioned in the second direction by the bottom walls of the array of wells slideably resting on bottom walls of the plurality of grooves or by the lower surface of the tape segment intermediate the array of wells abutting the upper side wall of the bottom plate that is intermediate the plurality of grooves.

In preferred forms, the ridges, the lower face of the top plate, and the upper side wall of the bottom plate define the space receiving the tape segment.

In preferred forms, each groove includes a bottom wall intermediate the upper and lower side walls of the bottom plate in the second direction. The bottom plate further includes a plurality of apertures each extending from the lower side wall through one of the bottom walls of the grooves. The apertures have a number and locations corresponding to the array of wells of the tape segment. The array of wells of the tape segment is aligned with the apertures in the second direction and viewable via the apertures when the tape segment is positioned relative to the bottom plate.

In preferred forms, each groove extends from the first end towards but spaced from the second end of the bottom plate. Thus, each groove includes an end wall intermediate the first and second ends of the bottom plate in the first direction and extending in the second direction. The end walls of the grooves position the tape segment relative to the bottom plate in the first direction when the leading column of the array of wells most distant to the first end of the bottom plate abuts the end walls of the plurality of grooves.

In other preferred forms, each groove extends between the first and second ends of the bottom plate. The top plate includes a plurality of holes each extending from the upper face through the lower face. The holes have a number and locations corresponding to the array of wells of the tape segment. The top plate further includes a cutout extending from the upper face through the lower face of the top plate and extending from the first end of the top plate towards but spaced from the holes in the first direction. The cutout extends between and spaced from two lateral edges of the top plate in the third direction. The tape segment includes a bar code on an end thereof. The bar code is aligned with the cutout in the second direction and viewable via the cutout. The array of wells of the tape segment is aligned with the holes in the second direction and viewable via the holes. The upper side wall of the bottom plate further includes a bar code reading area free of the grooves, and the bar code reading area is aligned with the cutout in the second direction to provide optical contrast.

The present invention will become clearer in light of the following detailed description of illustrative embodiments of this invention described in connection with the drawings.

DESCRIPTION OF THE DRAWINGS

The illustrative embodiments may best be described by reference to the accompanying drawings where:

FIG. 1 is a perspective view of a tape adaptor according to the preferred teachings of the present invention.

FIG. 2 is an exploded, perspective view of the tape adaptor of FIG. 1.

FIG. 3 is a top view of the tape adaptor of FIG. 1.

FIG. 4 is a bottom view of the tape adaptor of FIG. 1.

FIG. 5 is a front view of the tape adaptor of FIG. 1.

FIG. 6 is a left side view of the tape adaptor of FIG. 1.

FIG. 7 is a right side view of the tape adaptor of FIG. 1.

FIG. 8 is a perspective view of a tape adaptor of another embodiment according to the preferred teachings of the present invention.

FIG. 9 is an exploded, perspective view of the tape adaptor of FIG. 8.

FIG. 10 is a top view of the tape adaptor of FIG. 8.

FIG. 11 is a bottom view of the tape adaptor of FIG. 8.

FIG. 12 is a front view of the tape adaptor of FIG. 8.

FIG. 13 is a left side view of the tape adaptor of FIG. 8.

FIG. 16 is a bottom view of the tape adaptor of FIG. 14.

FIG. 17 is a front view of the tape adaptor of FIG. 14.

FIG. 18 is a right side view of the tape adaptor of FIG. 14.

Figure 15:
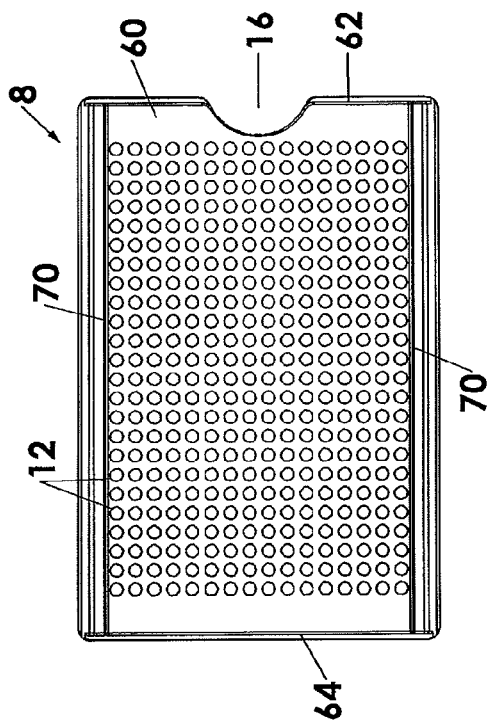
FIG. 15 is a top view of the tape adaptor of FIG. 14.

All figures are drawn for ease of explanation of the basic teachings of the present invention only; the extensions of the figures with respect to number, position, relationship, and dimensions of the parts to form the preferred embodiments will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

Where used in the various figures of the drawings, the same numerals designate the same or similar parts. Furthermore, when the terms "first", "second", "lower", "upper", "end", "longitudinal", "lateral", "spacing", "length", and similar terms are used herein, it should be understood that these terms have reference only to the structure shown in the drawings as it would appear to a person viewing the drawings and are utilized only to facilitate describing the invention.

DETAILED DESCRIPTION OF THE INVENTION

A tape adaptor according to the preferred teachings of the present invention is shown in the drawings and generally designated 8. Tape adaptor 8 is utilized to hold a tape segment 100 remaining on or cut from a continuous array tape 10 to mimic a microtiter plate. Tape segment 100 includes first and second ends 82 and 84 spaced in a first, longitudinal direction. Tape segment 100 further includes upper and lower surfaces 86 and 88 spaced in a second direction perpendicular to the first direction. Tape segment 100 further includes first and second edges 52 spaced in a third direction perpendicular to the first and second directions. Tape segment 100 further includes an array of wells 54 between first and second ends 82 and 84 and intermediate first and second edges 52. Array of wells 54 includes a plurality of columns 42 spaced in the first direction and a plurality of rows 44 spaced in the third direction. Each of the first and second edges 52 of tape segment 100 includes a plurality of tractor feed holes 56 formed in the first direction and spaced from array of wells 54 in the third direction. Further, tape segment 100 can be indexed utilizing at least one human or machine readable identification number 92 such as a bar code for pattern identification and/or for each array of wells 54. In the preferred form shown, two human or machine readable identification numbers 92 are formed on opposite sides of array of wells 54 and intermediate first and second edges 52. It can be appreciated that array of wells 54 of tape segment 100 can have differing patterns including, but not limited to, 8×12 wells with a spacing of 9 mm between centers, 16×24 wells with a spacing of 4.5 mm between centers, and 32×48 wells with a spacing of 2.25 mm between centers.

In the preferred forms shown, tape adaptor 8 includes a bottom plate 20 having first and second ends 22 and 24 spaced in the first direction. Tape adaptor 8 further includes upper and lower side walls 26 and 28 extending between first and second ends 22 and 24 and spaced in the second direction. Bottom plate 20 further includes a plurality of grooves 30 extending from upper side wall 26 towards but spaced from lower side wall 28. Grooves 30 are parallel to each other in the first direction and are spaced from each other in the third direction. Grooves 30 have a number corresponding to rows 44 of array of wells 54 of tape segment 100, with the number of grooves 30 and rows 44 being equal in the preferred form shown. Bottom plate 20 further includes first and second parallel, longitudinal edges 36 spaced from grooves 30 in the third direction, with grooves 30 intermediate first and second longitudinal edges 36. Each groove 30 further includes a bottom wall 32 intermediate upper and lower side walls 26 and 28 of bottom plate 20 in the second direction. In a preferred form shown in FIGS. 1-7, each groove 30 extends from first end 22 towards but spaced from second end 24 of bottom plate 20. Thus, each groove 30 includes an end wall 34 intermediate first and second ends 22 and 24 of bottom plate 20 in the first direction and extending in the second direction.

In the preferred forms shown, tape adaptor 8 further includes a top plate 60 having first and second ends 62 and 64 spaced in the first direction. Top plate 60 further includes upper and lower faces 66 and 68 extending between first and second ends 62 and 64 of top plate 60 and spaced in the second direction. In preferred forms, top plate 60 further includes a plurality of holes 12 each extending from upper face 66 through lower face 68. Holes 12 have a number and locations corresponding to array of wells 54 of tape segment 100 and in the preferred forms shown have sizes larger than openings of the wells 54. Top plate 60 further includes first and second lateral edges 70 on two sides of holes 12 and spaced from holes 12 in the third direction.

In preferred forms shown, upper side wall 26 of bottom plate 20 includes a first ridge 38 extending along first longitudinal edge 36 and extending away from lower side wall 28 of bottom plate 20 in the second direction, and extending from the first end 22 to the second end 24 of the bottom plate. Upper side wall 26 of bottom plate 20 further includes a second ridge 38 extending along second longitudinal edge 36 and extending away from lower side wall 28 of bottom plate 20 in the second direction, and extending from the first end 22 to the second end 24 of the bottom plate.

Figure 14:
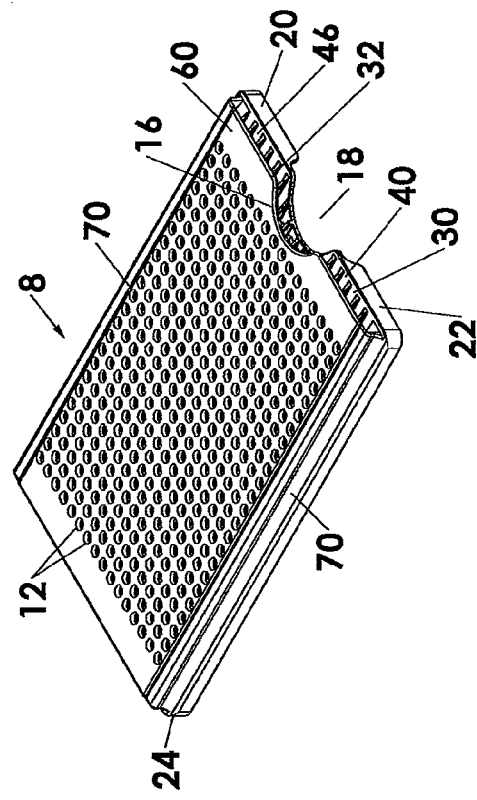
FIG. 14 is a perspective view of a tape adaptor of a further embodiment according to the preferred teachings of the present invention.

Top plate 60 is mounted to upper side wall 26 of bottom plate 20 defining a space 40 between upper side wall 26 of bottom plate 20 and lower face 68 of top plate 60 for receiving tape segment 100. Specifically, first and second ridges 38, lower face 68 of top plate 60, and upper side wall 26 of bottom plate 20 together define space 40 receiving tape segment 100 including first and second edges 52 in the preferred forms shown. A first slit 46 is formed between first end 62 of top plate 60 and first end 22 of bottom plate 20 and extending in the third direction providing access for tape segment 100 into space 40. Further, top plate 60 has a length the same as that of bottom plate 20 in the first direction in the forms shown in FIGS. 1-7 and FIGS. 14-18.

Further, in the preferred forms shown in FIGS. 1-13, each of first and second ridges 38 includes two fixing holes 80 spaced in the first direction. A plurality of fasteners 72 is extended through each of first and second lateral edges 70 of top plate 60 and each have a shank 76 beyond lower face 68. Shank 76 of each fastener 72 is engaged in one of fixing holes 80 of bottom plate 20.

Further, a second slit 48 is formed between second end 64 of top plate 60 and second end 24 of bottom plate 20 and extending in the third direction. In the preferred forms shown, second slit 48 is aligned with and spaced from first slit 46 in the first direction. Each of first and second ridges 38 extend proximate to the first end 22 of bottom plate 20 in the preferred form shown in FIGS. 1-7, creating a gap 58 between upper side wall 26 of bottom plate 20 and lower face 64 of top plate 60. Gaps 58 provide access to first and second edges 52 of tape segment 100.

Top and bottom plates 60 and 20 can be manufactured separately of suitable materials including but not limited to polystyrene, polypropylene, polycarbonate, cyclo-olefins and then assembled together such as by engaging fasteners 72 with fixing holes 80 in the preferred forms shown in FIGS. 1-13. However, top and bottom plates 60 and 20 can be coupled together via other suitable provisions including but not limited male/female coupling, bonding, or the like.

In preferred forms shown in FIGS. 8-18, each groove 30 extends between first and second ends 22 and 24 of bottom plate 20. Furthermore, bottom plate 20 includes a plurality of apertures 14 each extending from lower side wall 28 through one of bottom walls 32 of grooves 30. Apertures 14 have a number and locations corresponding to array of wells 54 of tape segment 100 and in the preferred form shown have sizes corresponding to wells 54. Furthermore, top plate 60 includes a cutout 16 extending from upper face 66 through lower face 68 and extending from first end 62 towards but spaced from holes 12 in the first direction. Cutout 16 extends between and is spaced from first and second lateral edges 70 in the third direction.

Cutout 16 in the preferred form shown in FIGS. 8-13 is rectangular in cross section. Further, bottom plate 20 is made of black anodized aluminum and includes a bar code reading area 90 on upper side wall 26 and aligned with cutout 16 in the second direction to provide optical contrast when reading a bar code on tape segment 100. Bar code reading area 90 in the preferred form shown is free of grooves 30 and of a size which is the same as cutout 16. Further, top plate 60 is shorter than bottom plate 20 in the first direction to make room for a guard plate on an automated tape cutter device having a cutter that cuts continuous array tape 10. To assist in automatic tape loading, bottom plate 20 longer than top plate 60 avoids a gap in the tape path when a holder is positioned next to the cutter. In manufacture, grooves 30 are first milled out in upper side wall 26 from adjacent first end 22. Then, upper side wall 26 is milled to include a recess of a depth to form bar code reading area 90.

In a preferred form shown in FIGS. 14-18, bottom plate 20 includes a cutout 18 extending from upper side wall 26 through lower side wall 28 and extending from first end 22 towards but spaced from apertures 14 of bottom plate 20 in the first direction. Cutout 18 extends between and is spaced from first and second longitudinal edges 36 in the third direction. Cutouts 16 and 18 in the form shown in FIGS. 14-18 are of identical size and shape, are arcuate in cross section, and are aligned with each other in the second direction to allow easy removal of tape segment 100. Tape adaptor 8 of the form shown in FIGS. 14-18 is formed as a single integral piece and is formed of aluminum by extrusion molding and then cut to a length. Specifically, first and second ridges 38 are integrally formed with first and second longitudinal edges 36 of bottom plate 20 and first and second lateral edges 70 of top plate 60. Holes 12, apertures 14, and cutouts 16 and 18 are then milled or drilled out of the extruded part.

Further, top plate 60 can include a stop 78 in the preferred form shown as locating pins extending between second end 64 of top plate 60 and second end 24 of bottom plate 20. Stop 78 can extend from at least one of upper side wall 26 of bottom plate 20 and lower face 68 of top plate 60 and into space 40 defined between upper side wall 26 of bottom plate 20 and lower face 68 of top plate 60 and within an extent of the plurality of grooves 30 in the third direction for abutting tape segment 100. Furthermore, stop 78 can have other forms, shapes, and numbers. As an example, stop 78 can be in the form of a plate abutting and stopping an end of continuous array tape 10 or tape segment 100. Further, tape adaptor 8 of FIGS. 14-18 can be formed without stop 78 to allow continuous array tape 10 or tape segment 100 to pass through second slit 48, and positioning of continuous array tape 10 or tape segment 100 relative to tape adaptor 8 can be controlled by tractor feed holes 56.

Although bottom plate 20 in the preferred forms shown in FIGS. 1-18 includes a plurality of grooves 30 each receiving a row of the array of wells 54, bottom plate 20 does not have to include grooves 30 or can include grooves 30 of differing configurations, and tape segment 100 can be positioned by holding the bottom walls of array of wells 54 against the bottom walls 32 of the grooves and/or the upper side 26 of bottom plate 20. As an example, bottom plate 20 can include only one groove 30 wide enough for array of wells 54 to save costs in making tape adaptor 8.

Now that the basic construction of tape adaptors 8 of the preferred teachings of the present invention has been explained, the use and some of the advantages of tape adaptors 8 can be set forth and appreciated. Tape adaptors 8 are utilized to hold tape segment 100 remaining on or cut from continuous array tape 10 to mimic a microtiter plate. In an example, continuous array tape 10 is flexible and made of embossable, thermo-conductive, and low mass material and fed from a supply roll by a tractor drive. Continuous array tape 10 includes tractor feed holes 56 for coupling with sprockets of the tractor drive. Tractor feed holes 56 allow automatic feeding of continuous array tape 10 with desired travel, so that continuous array tape 10 can be positioned in a desired location. Furthermore, continuous array tape 10 includes a plurality of tape segments 100 with arrays of wells 54 of tape segments 100 spaced from each other along the first direction and intermediate tractor feed holes 56.

In use of tape adaptor 8 according to the teachings of the present invention, tape adaptor 8 is placed in the feeding path of continuous array tape 10, and continuous array tape 10 is fed through first slit 46 into space 40. Rows 44 of an array of wells 54 of a tape segment 100 of continuous array tape 10 are slideably received in grooves 30 of bottom plate 20, with each row 44 of an array of wells 54 of tape segment 100 of continuous array tape 10 slideably received in one of grooves 30 of bottom plate 20 in the preferred forms shown. Continuous array tape 10 is stopped when it is fed in the first direction through a predetermined travel such as when a leading column 42 of array of wells 54 most distant to first end 22 of bottom plate 20 abuts end walls 34 of grooves 30 in FIGS. 1-7, due to tractor feed holes 56 allowing automatic feeding of continuous array tape 10 with desired travel, when continuous array tape 10 engages with stop 78, or the like. When tape segment 100 is positioned relative to tape adaptor 8, an array of wells 54 of tape segment 100 is aligned with holes 12 of top plate 60 in the second direction and viewable via holes 12 in the forms shown in FIGS. 1-18. In preferred forms shown in FIGS. 8-18, array of wells 54 of tape segment 100 is aligned with holes 12 of top plate 60 and apertures 14 of bottom plate 20 in the second direction and viewable via holes 12 and apertures 14 when tape segment 100 is positioned relative to tape adaptor 8. Then, continuous array tape 10 can be cut by a cutter device to leave tape segment 100 received in space 40. A microtiter plate including tape adaptor 8 and tape segment 100 held by tape adaptor 8 is, thus, made. A new adaptor can be moved to or placed in the feeding path of continuous array tape 10, and the procedure is repeated to make another microtiter plate.

In the preferred forms shown, both first and second edges 52 of tape segment 100 slide on first and second ridges 38 of bottom plate 20 during feeding of continuous tape array 100. When tape segment 100 is disconnected from the tape tractor drive such as after cutting, tape segment 100 can be positioned in the first direction in tape adaptor 8 by friction between the first and second edges 52 of tape segment 100 and the first and second ridges 38 and in the third direction by the first and second edges 52 of tape segment 100 being sandwiched between the first and second ridges 38 due to close tolerance therebetweeen. Further, tape segment 100 can be positioned in the second direction by bottom walls of array of wells 54 that slideably rest on bottom walls 32 of grooves 30 or by lower surface 88 of tape segment 100 intermediate array of wells 54 abutting upper side wall 26 of bottom plate 20 intermediate grooves 30. It should be appreciated that support by the upper side wall 26 intermediate grooves 30 allows tape adaptor 8 to receive tape segments 100 having array of wells 54 with differing depths.

Tape adaptors 8 according to the teachings of the present invention can be used in other ways. As an example, tape segment 100 can be cut from continuous array tape 10 before inserting into tape adaptor 8 via first slit 46. If desired, tape segment 100 can be removed from tape adaptor 8 so that it can be used again, saving the costs, with first end 82 of tape segment 10 outside of first slit 46 and cutouts 16 and 18 allowing easy removal of tape segment 100 after testing. In another example, continuous array tape 10 is inserted through first slit 46 into tape adaptor 8, removed from tape adaptor 8 after testing, and then cut, allowing a new array of wells 54 to be inserted into tape adaptor 8 when continuous array tape 10 is again inserted. Additionally, in use of tape adaptor 8 shown in FIGS. 8-13 or FIGS. 14-18 without stop 78, continuous array tape 10 or tape segment 100 may extend beyond tape adaptor 8 via second slit 48, with friction and/or tractor feed holes 56 retaining continuous array tape 10 or tape segment 100 in place. Furthermore, after testing and after moving through second slit 48 of tape adaptor 8, continuous array tape 10 can be left as a continuous strip and then rerolled on a spool or could be cut into segments at that time.

The microtiter plates formed by tape segments 100 and tape adaptors 8 according to the teachings of the present invention can be utilized on existing equipment for microtiter plates and conform to the Society of Biomolecular Sciences published microplate standards. Since array of wells 54 of tape segment 100 can be seen via holes 12 of top plate 60 or apertures 14 of bottom plate 20, optical reading of the reagents or samples in array of wells 54 of tape segment 100 can be carried out from top or bottom of tape adaptor 8.

Tape adaptors 8 according to the teachings of the present invention may or may not be equipment specific. Specifically, tape adaptors 8 according to the teachings of the present invention can be utilized with different equipment or machines including but not limited to of a commercially available type. However, tape adaptors 8 according to the teachings of the present invention can have a specific specification for use with specific equipment or machines if desired. As an example, tape adaptors 8 shown in FIGS. 1-7, FIGS. 8-13, and FIGS. 14-18 have different shapes at a bottom portion of bottom plate 20, allowing use of tape adaptors 8 with differing machines for various purposes.

Now that the basic teachings of the present invention have been explained, many extensions and variations will be obvious to one having ordinary skill in the art. It can be appreciated that in use of tape adaptors 8 such as shown in FIGS. 1-7 and FIGS. 14-18, continuous array tape 10 or tape segment 100 does not have to extend beyond tape adaptor 8 via second slit 48. In this case, tape adaptors 8 of FIGS. 1-7 and FIGS. 14-18 do not have to include second slit 48.

Further, the relative sizes between array of wells 54 and holes 12 and/or apertures 14 can be varied according to the teachings of the present invention. Specifically, holes 12 and apertures 14 can be sized to correspond to more than one well 54 and could have regular shapes such as circular, oval, rectangular, or FIG. 8 shapes or could have irregular shapes. Similarly, apertures 14 are shown in the preferred forms as having the same shape and sizes as holes 12, apertures 14 could have differing shapes and sizes according to the teachings of the present invention. Additionally, although array of wells 54 and holes 12 as shown are formed in rows and columns of equal spacing, array of wells 54 and holes 12 according to the teachings of the present invention could have different patterns than shown.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

The invention claimed is:

1. A microtiter plate comprising, in combination:
   a bottom plate having first and second ends spaced in a first direction and upper and lower side walls extending between the first and second ends, with the upper and lower side walls spaced in a second direction perpendicular to the first direction, with the bottom plate further including first and second longitudinal edges extending between the first and second ends and spaced in a third direction perpendicular to the first and second directions, a first ridge extending from the first longitudinal edge and extending away from the lower side wall of the bottom plate in the second direction, and extending substantially from the first end to the second end, and a second ridge extending from the second longitudinal edge and extending away from the lower side wall of the bottom plate in the second direction, and extending substantially from the first end to the second end, with the first and second ridges being spaced in the third direction;

a top plate including first and second ends spaced in the first direction and upper and lower faces extending between the first and second ends of the top plate, with the upper and lower faces spaced in the second direction, with the top plate abutting with and mounted to the first and second ridges of the bottom plate, with a space defined between the upper side wall of the bottom plate and the lower face of the top plate, with a first slit formed between the first end of the top plate and the first end of the bottom plate and extending in the third direction between the first and second ridges; and a tape segment received in the space and including first and second ends spaced in the first direction, with the tape segment further including an array of wells between the first and second ends of the tape segment, with the array of wells including a plurality of columns spaced in the first direction and a plurality of rows spaced in the third direction, with the tape segment further including first and second edges on two sides of the array of wells and spaced from the array of wells in the third direction, with the tape segment positioned relative to at least one of the top and bottom plates with the first slit extending in the third direction for an extent generally equal to and for slideably receiving the first and second edges of the tape segment, with the first ridge extending along the first longitudinal edge substantially from the first end to the second end, with the second ridge extending along the second longitudinal edge substantially from the first end to the second end, and with the tape segment slideably extending through the first slit in the first direction into the space with the first and second edges of the tape segment slideable on the first and second ridges of the bottom plate.

2. The microtiter plate as claimed in claim 1, with the bottom plate further including at least one groove extending from the upper side wall towards but spaced from the lower side wall in the second direction, with the at least one groove extending from the first end, with said at least one groove being intermediate and spaced from the first and second longitudinal edges in the third direction, with said at least one groove having a bottom wall intermediate the upper and lower side walls of the bottom plate in the second direction, with each of the wells of the tape segment having a bottom wall, with the array of wells of the tape segment slideably received in the first direction in said at least one groove with the bottom walls of the array of wells slideably resting on the bottom wall of said at least one groove, positioning the tape segment in the second direction, with said at least one groove including a plurality of grooves parallel to each other in the first direction and spaced from each other in the third direction, with the plurality of grooves having a number corresponding to the plurality of rows of the array of wells of the tape segment, with the array of wells of the tape segment received in the plurality of grooves, and with the plurality of rows of the array of wells of the tape segment received in the plurality of grooves with the bottom walls of the array of wells slideably resting on the bottom walls of said plurality of grooves.

3. The microtiter plate as claimed in claim 1, with the bottom plate further including a plurality of grooves extending from the upper side wall towards but spaced from the lower side wall in the second direction, with the plurality of grooves extending from the first end, with the plurality of grooves being intermediate the first and second longitudinal edges, with plurality of grooves parallel to each other in the first direction and spaced from each other in the third direction, with the plurality of grooves having a number corresponding to the plurality of rows of the array of wells of the tape segment, with each of the plurality of grooves having a bottom wall intermediate the upper and lower side walls of the bottom plate in the second direction, with the array of wells of the tape segment slideably received in the first direction in the plurality of grooves, and with a lower surface of the tape segment intermediate the array of wells abutting the upper side wall of the bottom plate intermediate the plurality of grooves, positioning the tape segment in the second direction.

4. The microtiter plate as claimed in claim 3, further comprising:

a stop extending from at least one of the upper side wall of the bottom plate and the lower face of the top plate and into the space defined between the upper side wall of the bottom plate and the lower face of the top plate and within an extent of the plurality of grooves in the third direction, with the stop abutting the second end of the tape segment to position the tape segment relative to one of the top and bottom plates, with the plurality of grooves extending between first and second ends of the bottom plate.

5. The microtiter plate as claimed in claim 3, with each of the plurality of grooves extending from the first end towards but spaced from the second end of the bottom plate, with each of the plurality of grooves of the bottom plate including an end wall intermediate the first and second ends of the bottom plate in the first direction and extending in the second direction, with one of the plurality of columns of the array of wells most distant to the first end of the bottom plate abutting the end walls of the plurality of grooves of the bottom plate, positioning the tape segment in the first direction, with the bottom plate further including a plurality of apertures each extending from the lower side wall through the bottom walls of the plurality of the grooves, with the plurality of apertures having a number and locations corresponding to the array of wells, and with the array of wells of the tape segment being aligned with the plurality of apertures in the second direction and viewable via the plurality of apertures.

6. The microtiter plate as claimed in claim 1, with the top plate further including a plurality of holes each extending from the upper face through the lower face, with the plurality of holes having a number and locations corresponding to the array of wells, with the array of wells of the tape segment being aligned with the plurality of holes in the second direction and viewable via the plurality of holes, with each of the first and second ridges extending proximate to the first end of the bottom plate, with gaps created between the upper side wall of the bottom plate and the lower face of the top plate and between the first end of the bottom plate and the first and second ridges with the top plate abutting with and mounted to the first and second ridges, and with the gaps providing access to the first and second edges of the tape segment.

7. The microtiter plate as claimed in claim 1, with the top plate further including a cutout extending from the upper face through the lower face of the top plate and extending from the first end of the top plate towards but spaced from the second end of the top plate in the first direction, with the cutout extending between and spaced from the first and second ridges in the third direction with the top plate abutting with and mounted to the first and second ridges, with the tape segment further including a bar code on one of the first and second ends of the tape segment, with the bar code being aligned with the cutout in the second direction and viewable via the cutout with the top plate abutting with and mounted to the first and second ridges, with the upper side wall of the bottom plate further including a bar code reading area free of the plurality of grooves, and with the bar code reading area aligned with the cutout and the bar code in the second direction.

8. A microtiter plate comprising, in combination:
a bottom plate having first and second ends spaced in a first direction and upper and lower side walls extending between the first and second ends, with the upper and lower side walls spaced in a second direction perpendicular to the first direction, with the bottom plate further including a plurality of grooves extending from the upper side wall towards but spaced from the lower side wall, with the plurality of grooves extending from the first end, with the plurality of grooves parallel to each other in the first direction and spaced from each other in a third direction perpendicular to the first and second directions,
with the bottom plate further including first and second longitudinal edges spaced from the plurality of grooves in the third direction, with the plurality of grooves being intermediate the first and second longitudinal edges, with the upper side wall of the bottom plate further including a first ridge extending along the first longitudinal edge and extending away from the lower side wall of the bottom plate in the second direction, and extending substantially from the first end to the second end, with the upper side wall of the bottom plate further including a second ridge extending along the second longitudinal edge and extending away from the lower side wall of the bottom plate in the second direction, and extending substantially from the first end to the second end, with the first and second ridges being spaced in the third direction,
a top plate including first and second ends spaced in the first direction and upper and lower faces extending between the first and second ends of the top plate, with the upper and lower faces spaced in the second direction, with the top plate mounted to the upper side wall of the bottom plate, with a space defined between the upper side wall of the bottom plate and the lower face of the top plate, with a first slit formed between the first end of the top plate and the first end of the bottom plate and extending in the third direction; and
a tape segment received in the space and including first and second ends spaced in the first direction, with the tape segment further including an array of wells between the first and second ends of the tape segment, with the array of wells including a plurality of columns spaced in the first direction and a plurality of rows spaced in the third direction and having a number corresponding to that of the plurality of grooves, with the tape segment further including first and second edges on two sides of the array of wells and spaced from the array of wells in the third direction, with the tape segment positioned relative to at least one of the top and bottom plates in the first direction, with the first slit extending in the third direction for an extent for slideably receiving the first and second edges of the tape segment, with the tape segment slideably extending through the first slit in the first direction into the space, and with the plurality of rows of the array of wells of the tape segment slideably received in the first direction in the plurality of grooves of the bottom plate, positioning the array of wells of the tape segment relative to the bottom plate in the third direction.

9. The microtiter plate as claimed in claim 8, further comprising:
a stop extending from at least one of the upper side wall of the bottom plate and the lower face of the top plate and into the space defined between the upper side wall of the bottom plate and the lower face of the top plate and within an extent of the plurality of grooves in the third direction, with the plurality of grooves extending between first and second ends of the bottom plate, and with the stop abutting the second end of the tape segment to position the tape segment relative to one of the top and bottom plates.

10. The microtiter plate as claimed in claim 8, with each of the plurality of grooves extending from the first end towards but spaced from the second end of the bottom plate, with each of the plurality of grooves of the bottom plate including an end wall intermediate the first and second ends of the bottom plate in the first direction and extending in the second direction, with one of the plurality of columns of the array of wells most distant to the first end of the bottom plate abutting the end walls of the plurality of grooves of the bottom plate, positioning the tape segment in the first direction,
with the first and second ridges, the lower face of the top plate, and the upper side wall of the bottom plate defining the space receiving the tape segment, with gaps created between the upper side wall of the bottom plate and the lower face of the top plate and between the first end of the bottom plate and the first and second ridges with the top plate abutting with and mounted to the first and second ridges, and with the gaps providing access to the first and second edges of the tape segment,
with the top plate further including a plurality of holes each extending from the upper face through the lower face, with the plurality of holes having a number and locations corresponding to the array of wells, with the array of wells of the tape segment being aligned with the plurality of holes in the second direction and viewable via the plurality of holes,
with each of the plurality of grooves including a bottom wall intermediate the upper and lower side walls of the bottom plate in the second direction, with the bottom plate further including a plurality of apertures each extending from the lower side wall through one of the bottom walls of the plurality of the grooves, with the plurality of apertures having a number and locations corresponding to the array of wells, with the array of wells of the tape segment being aligned with the plurality of apertures in the second direction and viewable via the plurality of apertures,
with the tape segment further including a bar code on one of the first and second ends of the tape segment, with the top plate including a cutout aligned with the bar code, with the bar code being aligned with the cutout in the second direction and viewable via the cutout with the top plate abutting with and mounted to the first and second ridges, with the upper side wall of the bottom plate further including a bar code reading area free of the plurality of grooves, and with the bar code reading area aligned with the cutout and the bar code in the second direction.

11. A tape adaptor comprising, in combination:
a bottom plate having first and second ends spaced in a first direction and upper and lower side walls extending between the first and second ends, with the upper and lower side walls spaced in a second direction perpendicular to the first direction, with the bottom plate further including first and second longitudinal edges extending between the first and second ends and spaced in a third direction perpendicular to the first and second directions, a first ridge extending from the first longitudinal edge and extending away from the lower side wall of the bottom plate in the second direction and extending substantially from the first end to the second end, and a second ridge extending from the second longitudinal edge and extending away from the lower side wall of the bottom plate in the second direction and extending substantially from the first end to the second end, with the first and second ridges being spaced in the third direction; and a top plate including first and second ends spaced in the first direction and upper and lower faces extending between the first and second ends of the top plate, with the upper and lower faces spaced in the second direction, with the top plate abutting with and mounted to the first and second ridges of the bottom plate, with a space defined between the upper side wall of the bottom plate and the lower face of the top plate, with the space adapted to receive a tape segment including an array of wells having a plurality of columns spaced in the first direction and a plurality of rows spaced in the third direction with the top plate abutting with and mounted to the first and second ridges, with the tape segment further including first and second edges on two sides of the array of wells and spaced from the array of wells in the third direction, with a first slit formed between the first end of the top plate and the first end of the bottom plate and extending in the third direction, with the tape segment positioned relative to at least one of the top and bottom plates with the first slit extending in the third direction for an extent generally equal to and for slideably receiving the first and second edges of the tape segment, and with the tape segment being adapted to slideably extend in the first direction through the first slit into the space in the first direction with the first and second edges of the tape segment slideably resting on the first and second ridges of the bottom plate.

12. The tape adaptor as claimed in claim 11, with the bottom plate further including at least one groove extending from the upper side wall towards but spaced from the lower side wall in the second direction, with the at least one groove extending from the first end, with said at least one groove being intermediate and spaced from the first and second longitudinal edges in the third direction, with said at least one groove having a bottom wall intermediate the upper and lower side walls of the bottom plate in the second direction, with said at least one groove adapted to receive the plurality of rows of the array of wells of the tape segment with bottom walls of the array of wells slideably resting on the bottom wall of said at least one groove to position the tape segment in the second direction, with said at least one groove including a plurality of grooves parallel to each other in the first direction and spaced from each other in the third direction, with the plurality of grooves having a number corresponding to the plurality of rows of the array of wells of the tape segment, and with the array of wells of the tape segment received in the plurality of grooves with bottom walls of the array of wells slideable on the bottom walls of said plurality of grooves.

13. The tape adaptor as claimed in claim 11, with the bottom plate further including a plurality of grooves extending from the upper side wall towards but spaced from the lower side wall in the second direction, with the plurality of grooves extending from the first end, with the plurality of grooves being intermediate the first and second longitudinal edges, with plurality of grooves parallel to each other in the first direction and spaced from each other in the third direction, with the plurality of grooves having a number corresponding to the plurality of rows of the array of wells of the tape segment, with each of the plurality of grooves having a bottom wall intermediate the upper and lower side walls of the bottom plate in the second direction, with the plurality of grooves adapted to receive the array of wells of the tape segment, and with a lower surface of the tape segment intermediate the array of wells abutting the upper side wall of the bottom plate intermediate the plurality of grooves to position the tape segment in the second direction.

14. The tape adaptor as claimed in claim 13, further comprising:
a stop extending from at least one of the upper side wall of the bottom plate and the lower face of the top plate and into the space defined between the upper side wall of the bottom plate and the lower face of the top plate and within an extent of the plurality of grooves in the third direction, with the plurality of grooves extending between first and second ends of the bottom plate.

15. The tape adaptor as claimed in claim 13, with each of the plurality of grooves extending from the first end towards but spaced from the second end of the bottom plate, with each of the plurality of grooves of the bottom plate including an end wall intermediate the first and second ends of the bottom plate in the first direction and extending in the second direction, and with the end walls of the plurality of grooves positioning the tape segment relative to the bottom plate in the first direction when one of the plurality of columns of the array of wells most distant to the first end of the bottom plate abuts the end walls of the plurality of grooves.

16. The tape adaptor as claimed in claim 12, with the bottom plate further including a plurality of apertures each extending from the lower side wall through one of the bottom walls of the plurality of the grooves, with the plurality of apertures having a number and locations corresponding to the array of wells of the tape segment, with the array of wells of the tape segment being aligned with the plurality of apertures in the second direction and viewable via the plurality of apertures,
with gaps created between the upper side wall of the bottom plate and the lower face of the top plate and between the first end of the bottom plate and the first and second ridges with the top plate abutting with and mounted to the first and second ridges, with the gaps providing access to two edges of the tape segment spaced from the array of wells in the third direction,
with the top plate further including a cutout extending from the upper face through the lower face of the top plate and extending from the first end of the top plate towards but spaced from the second end of the top plate in the first direction, with the cutout extending between and spaced from the first and second ridges in the third direction with the top plate abutting with and mounted to the first and second ridges, and
with the upper side wall of the bottom plate further including a bar code reading area, with the bar code reading area aligned with the cutout, with the bottom plate further including a cutout extending from the upper side wall through the lower side wall of the bottom plate and extending from the first end of the bottom plate towards but spaced from the second end of the bottom plate, and with the cutout of the bottom plate aligned with and spaced from the cutout of the top plate in the second direction.

17. The tape adaptor as claimed in claim 11, with the top plate further including a plurality of holes each extending from the upper face through the lower face, with the plurality of holes having a number and locations corresponding to the array of wells of the tape segment, and with the array of wells of the tape segment being aligned with the plurality of holes in the second direction and viewable via the plurality of holes.

18. A tape adaptor comprising, in combination:
a bottom plate having first and second ends spaced in a first direction and upper and lower side walls extending between the first and second ends, with the upper and lower side walls spaced in a second direction perpendicular to the first direction; and
a first ridge extending from the lower side wall of the bottom plate in the second direction, and extending substantially from the first end to the second end, with the upper side wall of the bottom plate further including a second ridge extending along the second longitudinal edge and extending away from the lower side wall of the bottom plate in the second direction, and extending substantially from the first end to the second end,
a top plate including first and second ends spaced in the first direction and upper and lower faces extending between the first and second ends of the top plate, with the upper and lower faces spaced in the second direction, with the top plate mounted to the upper side wall of the bottom plate, with a space defined between the upper side wall of the bottom plate and the lower face of the top plate, with the space adapted to receive a tape segment including an array of wells having a plurality of columns spaced in the first direction and a plurality of rows spaced in the third direction and having a number corresponding to that of the plurality of grooves, with a first slit formed between the first end of the top plate and the first end of the bottom plate and extending in the third direction, with the top plate mounted to the bottom plate, with the bottom plate further including a plurality of grooves extending from the upper side wall towards but spaced from the lower side wall, with the plurality of grooves extending from the first end, with the plurality of grooves parallel to each other in the first direction and spaced from each other in a third direction perpendicular to the first and second directions, with the first slit extending in the third direction for an extent for slideably receiving the first and second edges of the tape segment, with the tape segment being adapted to slideably extend through the first slit into the space in the first direction and positioned relative to at least one of the top and bottom plates in the first direction, and with the plurality of rows of the array of wells of the tape segment adapted to be received in the first direction in the plurality of grooves of the bottom plate to position the array of wells of the tape segment relative to the bottom plate in the third direction.

19. The tape adaptor as claimed in claim 18, further comprising:
a stop extending from at least one of the upper side wall of the bottom plate and the lower face of the top plate and into the space defined between the upper side wall of the bottom plate and the lower face of the top plate and within an extent of the plurality of grooves in the third direction, with the plurality of grooves extending between first and second ends of the bottom plate.

20. The tape adaptor as claimed in claim 18, with each of the plurality of grooves extending from the first end towards but spaced from the second end of the bottom plate, with each of the plurality of grooves of the bottom plate including an end wall intermediate the first and second ends of the bottom plate in the first direction and extending in the second direction, with the end walls of the plurality of grooves positioning the tape segment relative to the bottom plate in the first direction when one of the plurality of columns of the array of wells most distant to the first end of the bottom plate abuts the end walls of the plurality of grooves,
with the bottom plate further including first and second longitudinal edges spaced from the plurality of grooves in the third direction, with the plurality of grooves being intermediate the first and second longitudinal edges, with the upper side wall of the bottom plate including the first ridge extending along the first longitudinal edge, with the upper side wall of the bottom plate including the second ridge extending along the second longitudinal edge, with the first and second ridges being spaced in a third direction with the top plate abutting with and mounted to the first and second ridges, with the first and second ridges, the lower face of the top plate, and the upper side wall of the bottom plate defining the space receiving the tape segment,
with each of the first and second ridges extending proximate the first end of the bottom plate, with gaps created between the upper side wall of the bottom plate and the lower face of the top plate and between the first end of the bottom plate and the first and second ridges with the top plate abutting with and mounted to the first and second ridges, with the gaps providing access to two edges of the tape segment spaced from the array of wells in the third direction, with the top plate further including first and second lateral edges spaced in the third direction,
with the top plate further including a cutout extending from the upper face through the lower face of the top plate and extending from the first end of the top plate towards but spaced from the second end of the top plate in the first direction, with the cutout extending between and spaced from the first and second lateral edges in the third direction with the top plate abutting with and mounted to the first and second ridges, with the upper side wall of the bottom plate further including a bar code reading area free of the plurality of grooves, and with the bar code reading area aligned with the cutout, with the bottom plate further including a cutout extending from the upper side wall through the lower side wall of the bottom plate and extending from the first end of the bottom plate towards but spaced from the second end of the bottom plate, with the cutout of the bottom plate aligned with and spaced from the cutout of the top plate in the second direction, and
with the top plate further including a plurality of holes each extending from the upper face through the lower face, with the plurality of holes having a number and locations corresponding to the array of wells of the tape segment, with the array of wells of the tape segment being aligned with the plurality of holes in the second section and viewable via the plurality of holes, with each of the plurality of grooves including a bottom wall intermediate the upper and lower side walls of the bottom plate in the second direction, with the bottom plate further including a plurality of apertures each extending from the lower side wall through one of the bottom walls of the plurality of the grooves, with the plurality of apertures having a number and locations corresponding to the array of wells of the tape segment, and with the array of wells of the tape segment being aligned with the plurality of apertures in the second direction and viewable via the plurality of apertures.

* * * * *